United States Patent
Tsai et al.

(10) Patent No.: US 10,912,499 B2
(45) Date of Patent: Feb. 9, 2021

(54) DETECTING APPARATUS BASED ON IMAGE FOR BLOOD GLUCOSE CONCENTRATION AND METHOD THEREOF

(71) Applicant: National Applied Research Laboratories, Taipei (TW)

(72) Inventors: Hsin-Yi Tsai, Taipei (TW); Kuo-Cheng Huang, Taipei (TW); Ching-Ching Yang, Taipei (TW); Tzu-Ting Wei, Taipei (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 831 days.

(21) Appl. No.: 15/633,648

(22) Filed: Jun. 26, 2017

(65) Prior Publication Data

US 2018/0085035 A1    Mar. 29, 2018

(30) Foreign Application Priority Data

Sep. 23, 2016  (TW) .............................. 105130832 A

(51) Int. Cl.
*A61B 5/1455*   (2006.01)
*A61B 5/01*     (2006.01)
*A61B 5/145*    (2006.01)
*A61B 5/00*     (2006.01)
*A61B 5/026*    (2006.01)

(52) U.S. Cl.
CPC ............ *A61B 5/1455* (2013.01); *A61B 5/015* (2013.01); *A61B 5/14532* (2013.01); *A61B 5/0082* (2013.01); *A61B 5/0261* (2013.01); *A61B 5/14551* (2013.01)

(58) Field of Classification Search
CPC .................................................... A61B 5/1455
See application file for complete search history.

(56) References Cited

U.S. PATENT DOCUMENTS

| 2003/0023152 A1* | 1/2003 | Abbink | A61B 5/0075 600/316 |
| 2005/0265585 A1* | 12/2005 | Rowe | G06K 9/00046 382/124 |

(Continued)

*Primary Examiner* — Daniel L Cerioni
*Assistant Examiner* — Yasmeen S Warsi
(74) *Attorney, Agent, or Firm* — Cheng-Ju Chiang

(57) ABSTRACT

The present invention provides a detecting apparatus based on image for detecting blood glucose concentration and method thereof. The detecting apparatus comprising a lighting device, an image capture device, a thermal imager and an operating device. The lighting device including a first wavelength of light source and a second wavelength of light source, configured to illuminate skin. The image capture device disposed above the lighting device, configured to capture a first image and a second image corresponding to the first wavelength of light source and the second wavelength of light source illuminated on the skin respectively. The thermal imager is configured to detect temperature of the skin. The operating device is connected to the lighting device, the image capture device and the thermal imager, configured to calculate blood glucose concentration according to the first image, the second image and the temperature.

15 Claims, 3 Drawing Sheets
(1 of 3 Drawing Sheet(s) Filed in Color)

(56) References Cited

U.S. PATENT DOCUMENTS

| | | | |
|---|---|---|---|
| 2008/0269580 A1* | 10/2008 | Balistreri | A61B 5/14532 600/328 |
| 2010/0210930 A1* | 8/2010 | Saylor | A61B 5/14532 600/323 |
| 2017/0071516 A1* | 3/2017 | Bhagat | A61B 5/14551 |

* cited by examiner

DETECTING APPARATUS BASED ON IMAGE FOR BLOOD GLUCOSE CONCENTRATION AND METHOD THEREOF

BACKGROUND OF THE INVENTION

1. Field of the Invention

The present invention relates to a detecting apparatus based on image for blood glucose concentration and method thereof, especially a non-invasive and imaging blood glucose concentration detecting device and method.

2. Description of the Prior Art

In modern illness, diabetes is generally known. The diabetes complication are quite much more, such as Hypoglycemia, Diabetic ketoacidosis, Hyperosmotic nonketotic diabetic coma, Cardiovascular disease, Chronic renal failure, Retinopathy, Neuropathy, and Microangiopathy. Since diabetes patients have no obvious symptoms in early stage, if the symptoms can be found and treated in the early stage, the above complications can be reduced. In addition, the medical cost also can be saved. Accordingly, it is important to detect and control patients' blood glucose concentration continuously.

General blood glucose concentration detector usually is an invasive detector, such as using lancet and test strip to get patient's blood, then determining the blood glucose concentration by electrochemical or photochemical way. However, in such way, the signal determination is easily interfered with not only other optical signals or inappropriate operation, but also easily causes patient's finger infection and the fear of acupuncture treatment. In addition, the disposable consumables are not eco-friendly.

SUMMARY OF THE INVENTION

Accordingly, one aspect of this present invention is to provide an image blood glucose concentration detecting apparatus. The detecting apparatus calculates the blood oxygen saturation through the skin images illuminated by red light and infrared light, then getting the blood glucose concentration converted by formulas to supply a large range distribution of the blood glucose concentration. It can be used as a reference for determining a precursor of diabetic peripheral circulation.

The detecting apparatus comprises a lighting device, an image capture device, a thermal imager and an operating device. The lighting device including a first wavelength of light source and a second wavelength of light source, configured to illuminate skin. The image capture device disposed above the lighting device, configured to capture a first image and a second image corresponding to the first wavelength of light source and the second wavelength of light source illuminated on the skin respectively. The thermal imager is configured to detect temperature of the skin. The operating device is connected to the lighting device, the image capture device and the thermal imager.

Wherein the operating device calculates the blood glucose concentration according to the first image, the second image and the temperature.

Another aspect of this present invention is to provide an image blood glucose concentration detecting method. The detecting method calculates the blood oxygen saturation through the images illuminated by red light and infrared light, then getting the blood glucose concentration converted by formulas to supply a large range distribution of the blood glucose concentration. It can be used as a reference for determining a precursor of diabetic peripheral circulation.

The detecting method comprises following steps: (A1) illuminating skin with different wavelength of light sources; (A2) capturing skin images corresponding to the light sources illuminated on the skin; (A3) detecting temperature of the skin; (A4) calculating blood oxygen saturation according to the skin images; (A5) transforming the blood oxygen saturation into partial pressure of blood oxygen and solubility of blood oxygen; and (A6) calculating blood glucose concentration.

Compared to the prior art, the detecting apparatus based on image for blood glucose concentration and method thereof in the present invention, providing a non-invasive blood glucose image information to improve correctness of the doctor's diagnosis. The way is much more fast and accurate, in addition, it is widely applicable to different skin color race.

BRIEF DESCRIPTION OF THE DRAWINGS

The present patent application file contains at least one drawing executed in color. Copies of this patent application publication with color drawing(s) will be provided by the Office upon request and payment of the necessary fee.

DETAILED DESCRIPTION OF THE PREFERRED EMBODIMENT

Figure 1:
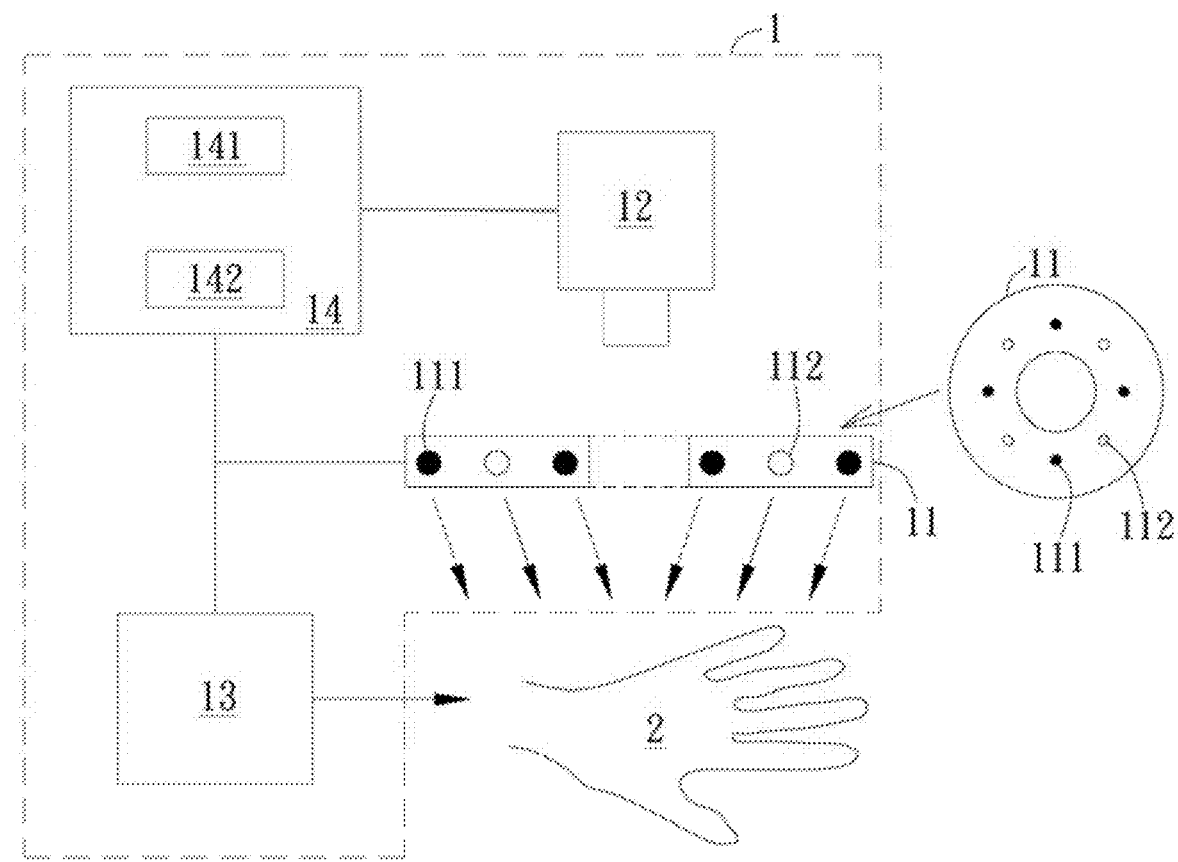
FIG. 1 is a block diagram of a detecting apparatus in one embodiment.

Please refer to FIG. 1. An image blood glucose concentration detecting apparatus 1 comprises a lighting device 11, an image capture device 12, a thermal imager 13 and an operating device 14. The operating device 14 is in connection with the lighting device 11, the image capture device 12 and the thermal imager 13, respectively. The lighting device 11 preferably includes a first wavelength of light source 111 and a second wavelength of light source 112. The first wavelength of light source 111 and the second wavelength of light source 112 can be LED light sources or the like. Wherein the two light sources 111 and 112 preferably have different wavelengths. In this embodiment, the first wavelength of light source 111 is a red light, the wavelength is 660 nm±20 nm. The second wavelength of light source 112 is an infrared light, the wavelength is 890 nm±20 nm. The lighting device 11 is preferably a circular type, but not limited thereto. In other embodiments, it also can be a rectangular type or other shapes, as long as the area corresponding to the image capture device 12 is easily to be captured and is not blocked. The two light sources 111 and 112 are preferably arranged in an interlaced manner, but not limited thereto. The main purpose is to uniform the lights.

The image capture device 12 in this embodiment is a device which has to capture the image illuminated by the first wavelength of light source 111 and the second wavelength of light source 112. The purpose is to avoid the two wavelengths from the lighting device 11 filtering. For instance, when the first wavelength of light source 111 and the second wavelength of light source 112 are red light and infrared light respectively, the image capture device 12 must capture the red light and infrared light. In other embodiment, the image capture device 12 can be a camera, a video camera, or the like.

It is noted that, in case the captured image affected by other ambient light, the image blood glucose concentration detecting apparatus 1 in this embodiment is preferably disposed in a darkroom or the like.

The operating device 14 can be a computer or other devices which have ability of calculating and storing. The operating device 14 preferably includes a control unit 141 (e.g. control circuit, controller) and an operating unit 142 (e.g. calculating circuit, processor). The control unit 141 is configured to control/switch the lighting device 11 to illuminate skin 2 with the red light and the infrared light by turns. That is, it controls/switches the first wavelength of light source 111 and the second wavelength of light source 112 to illuminate skin 2 with the red light and the infrared light by turns. The image capture device 12 is preferably disposed over the lighting device 11. When the first wavelength of light source 111 illuminates skin 2 with red light, the area where illuminated by red light on skin 2 is captured by the image capture device 12, and the image is defined as a first image. When the second wavelength of light source 112 illuminates skin 2 with infrared light, the area where illuminated by infrared light on skin 2 is captured by the image capture device 12, and the image is defined as a second image.

The thermal imager 13 is configured to detect the temperature of the skin 2. It is noted that detecting the skin 2 temperature can before or after capturing images. The temperature is used to calibrate the following calculating formula. The thermal imager 13 in this embodiment can be an infrared thermal imager, but not limited thereto. The operating unit 142 compares/analyzes the first image with the second image. Specifically, it compares/analyzes the light intensity information on the same position of two images. It is noted that, the operating unit 142 will use a white target as a standard reference while comparing/analyzing. The white target can be a white tape or the like, and disposed on the skin. The reason is that when the operating unit 142 calculates the blood oxygen saturation, it uses the ratio of incident light to reflected light. However, in this situation it cannot know the intensity of the incident light, so it calculates the intensity of the incident light by the reflected ratio and the reflected light intensity of the white target. Then it can get the incident light intensity information and the reflected light intensity of skin for calculating the blood oxygen saturation.

The operating unit 142 compares/analyzes the light intensity information on the same position of two images. Calculating the blood oxygen saturation by light intensity information on each position. Then converting the blood oxygen saturation into partial pressure of blood oxygen through following relationship:

$$S(p) = 102.5961 - \frac{101.84796}{1 + \left(\frac{p}{27.29198}\right)^{2.52764}}$$

wherein, S(p) is blood oxygen saturation, p is partial pressure of blood oxygen.

Then, converting the partial pressure of blood oxygen p into a solubility of blood oxygen $C_{gas}$ by the following relationship:

$$C_{gas} = \alpha \times P,$$

wherein p is partial pressure of blood oxygen, $C_{gas}$ is solubility of blood oxygen, and α is a coefficient. The coefficient α can be converted by the temperature detected from the thermal imager 13, the relationship is:
ln α=1.9685−0.018638T, wherein T is an absolute (Kevin) temperature. In this embodiment, take 33° C. as human skin temperature for calculating. Accordingly, a will be 7.753.

Further, converting the solubility of blood oxygen to get the blood glucose concentration through the following relationship:

$$C_g = \alpha - \beta C_{gas},$$

wherein $C_g$ is the blood glucose concentration, and α, β are coefficients. In this relationship, α=7.753, β=52.642. It is noted that the normal blood oxygen saturation in human is 90~99%. We can calculate the corresponding solubility of blood oxygen, and the corresponding blood glucose concentration is 4-6 mmol/L. Accordingly, a linear equation may be developed, then we can get β based on the above values.

In this embodiment, the above mathematical relationships may be developed into a mathematical analysis model. The model can be written in a storage device (e.g. memory) of the operating device 14 with software or firmware manner. When the operating device 14 receives images, temperatures and other information in need, it calculates or analyzes immediately through the model.

Accordingly, the detecting apparatus is non-invasive, the blood glucose concentration are calculated from the blood oxygen saturation which is evaluated through the skin image illuminated by the red light and the infrared light.

Figure 2:
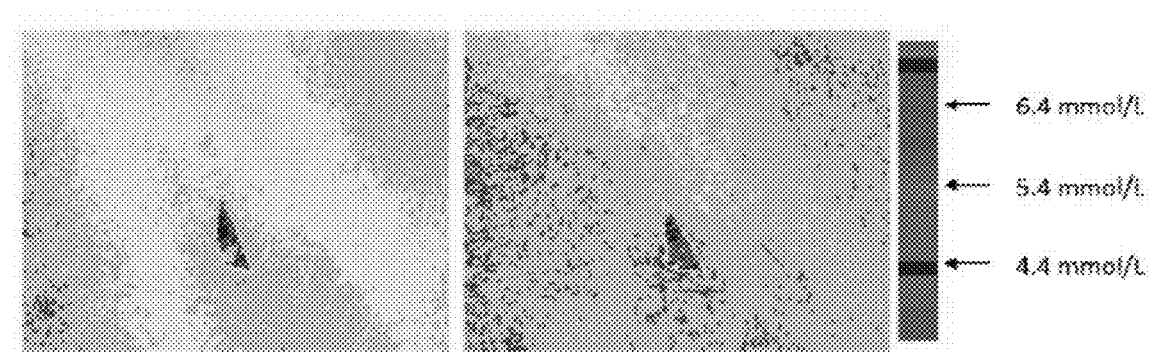
FIG. 2 is an image diagram of a blood glucose concentration distribution in one embodiment.

In another embodiment, the image blood glucose concentration detecting apparatus 1 further can develop a blood glucose concentration distributing image. As shown in FIG. 2, the blood glucose concentration distributing image clearly shows the variation of blood glucose concentration between the blood vessel and tissue. In FIG. 2, the different colors indicate different blood glucose concentration, respectively.

Figure 3:
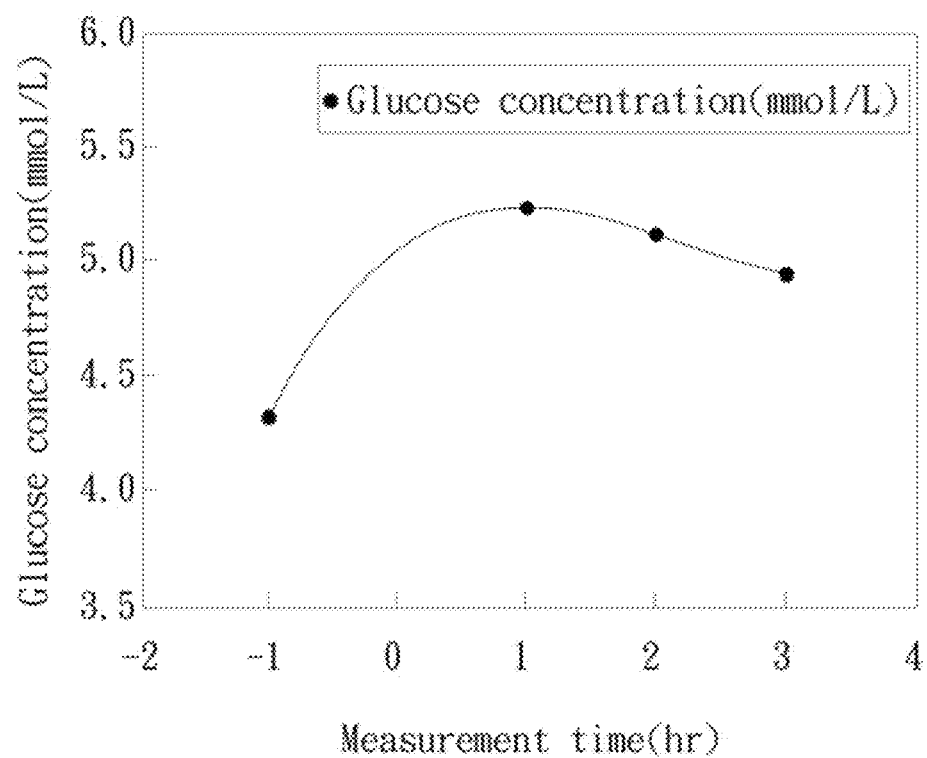
FIG. 3 is a graph of blood glucose concentration variation in one embodiment.

In addition, it also can provide the variation of blood glucose concentration value before and after diet. As shown in FIG. 3, it shows the variation of blood glucose concentration value one hour before ~three hours after diet.

Figure 4:
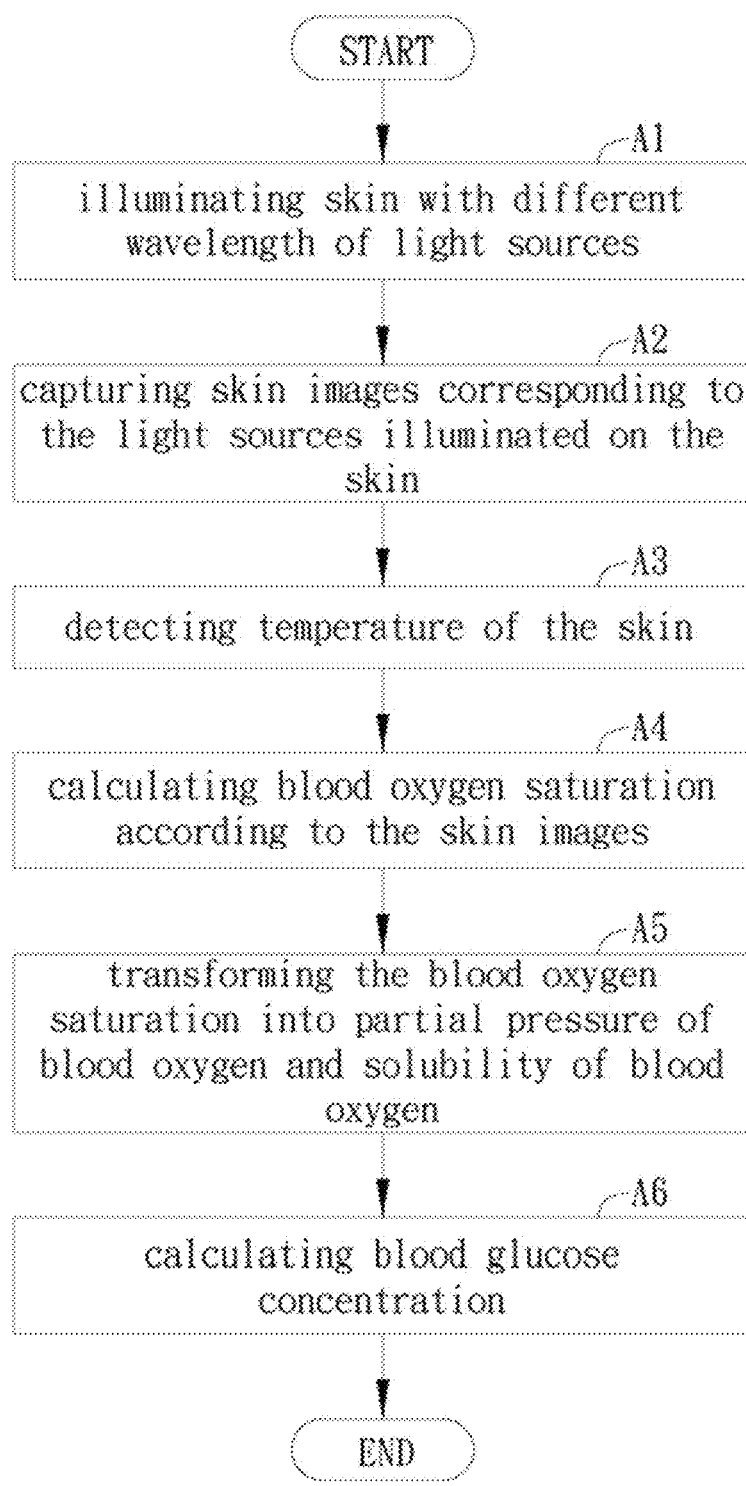
FIG. 4 is a flow chart of a detecting method in one embodiment.

Another aspect of the present invention provides an image blood glucose concentration detecting method, adapted to the image blood glucose concentration detecting apparatus 1. The detecting method is preferably performed in a darkroom. As shown in FIG. 4, The detecting method comprises the following steps: (A1) illuminating skin with different wavelength of light sources; (A2) capturing skin images corresponding to the light sources illuminated on the skin; (A3) detecting temperature of the skin; (A4) calculating blood oxygen saturation according to the skin images; (A5) transforming the blood oxygen saturation into partial pressure of blood oxygen and solubility of blood oxygen; and (A6) calculating blood glucose concentration.

In steps (A1) and (A2): the control unit 141 is configured to control/switch the lighting device 11 to illuminate skin 2 with the first wavelength of light source 111 (e.g. red light) and the second wavelength of light source 112 (e.g. infrared light) by turns. When the first wavelength of light source 111 illuminates skin 2 with red light, the area where illuminated by red light on skin 2 is captured by the image capture device 12, and the image is defined as a first image. When the second wavelength of light source 112 illuminates skin 2 with infrared light, the area where illuminated by infrared light on skin 2 is captured by the image capture device 12, and the image is defined as a second image.

In step (A3): using the thermal imager 13 to detect skin 2 temperature. It is noted that detecting the skin 2 temperature can before or after capturing images. The temperature is used to calibrate the following calculating formula.

In step (A4): the operating unit 142 compares/analyzes the first image with the second image. Specifically, it compares/analyzes the light intensity information on the same position of two images and calculates the blood oxygen saturation.

In step (A5): getting the partial pressure of blood oxygen and the solubility of blood oxygen by converting the blood oxygen saturation.

In step (A6): converting the solubility of blood oxygen into the blood glucose concentration.

Similarly, it may perform step (A7): generating a blood glucose concentration distributing image.

The converting process and the hardware detail are described in the above embodiment, no more tautology here.

Compared to the prior art, the detecting apparatus based on image for blood glucose concentration and method thereof in the present invention, providing a non-invasive blood glucose image information to improve correctness of the doctor's diagnosis. The way is much more fast and accurate, in addition, it is widely applicable to different skin color race.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An image blood glucose concentration detecting apparatus, comprising:
    a light device, including a light source that emits a light beam of a first wavelength to a skin, and a light source that emits a light beam of a second wavelength to the skin;
    an image capture device disposed above the lighting device, configured to the image capture device capturing a first image of the skin by receiving the light beam of the first wavelength reflected from the skin, and capturing a second image of the skin by receiving the light beam of the second wavelength reflected from the skin;
    a thermal imager detecting a temperature of the skin; and
    an operating device, connected to the lighting device, the image capture device and the thermal imager;
    wherein the operating device calculates a blood oxygen saturation according to the first image and the second image, and calculates a blood glucose concentration according to the blood oxygen saturation and the temperature.

2. The apparatus as claimed in claim 1, wherein the light source with the first wavelength is a red light, and the light source with the second wavelength is an infrared light.

3. The apparatus as claimed in claim 1, wherein the operating device comprises at least one control unit and an operating unit.

4. The apparatus as claimed in claim 1, wherein the operating device further comprises a mathematical analysis model, having a mathematical relationship:

$$S(p) = 102.59681 - \frac{101.84796}{1 + \left(\frac{p}{27.29198}\right)^{2.52764}}, C_{gas} = \alpha \times P, \text{ and}$$

$$C_g = \alpha - \beta C_{gas},$$

wherein, S(p) is blood oxygen saturation, p is partial pressure of blood oxygen, $C_{gas}$ is solubility of blood oxygen, $C_g$ is the blood glucose concentration, and $\alpha$, $\beta$ are coefficients.

5. The apparatus as claimed in claim 1, wherein the operating device generates a blood glucose concentration distributing image according to the first image, the second image and the temperature.

6. The apparatus as claimed in claim 2, wherein a wavelength of the first light source is 660nm±20nm, and a wavelength of the second light source is 890nm±20nm.

7. An image blood glucose concentration detecting method, adapted to the apparatus of claim 1, comprising following steps:
    (A1) emitting light beams of different wavelengths from a plurality of light sources to a skin;
    (A2) capturing images of the skin each respectively corresponding to each of the different wavelengths by receiving the light beams of different wavelengths reflected from the skin;
    (A3) detecting temperature of the skin;
    (A4) calculating blood oxygen saturation according to the images;
    (A5) transforming the blood oxygen saturation into partial pressure of blood oxygen and solubility of blood oxygen; and
    (A6) calculating blood glucose concentration.

8. The method as claimed in claim 7, further comprising following step:
    (A7) generating a blood glucose concentration distributing image.

9. The method as claimed in claim 7, wherein in the step (A5), calculating the blood oxygen saturation into partial pressure of blood oxygen and the solubility of blood oxygen according to following mathematical relationship:

$$S(p) = 102.59681 - \frac{101.84796}{1 + \left(\frac{p}{27.29198}\right)^{2.52764}}, \text{ and } C_{gas} = \alpha \times P,$$

wherein S(p) is blood oxygen saturation, p is partial pressure of blood oxygen, $C_{gas}$ is solubility of blood oxygen, and $\alpha$ is a coefficient.

10. The method as claimed in claim 9, wherein in the step (A6), calculating blood glucose concentration by following mathematical relationship:

$$C_g = \alpha - C_{gas},$$

wherein $C_g$ is the blood glucose concentration, and $\alpha$, $\beta$ are coefficients.

11. An image blood glucose concentration detecting method, adapted to the apparatus of claim 2, comprising following steps:
    (A1) emitting light beams of different wavelengths from a plurality of light sources to a skin;
    (A2) capturing images of the skin each respectively corresponding to each of the different wavelengths by receiving the light beams of different wavelengths reflected from the skin;

(A3) detecting temperature of the skin;
(A4) calculating blood oxygen saturation according to the images;
(A5) transforming the blood oxygen saturation into partial pressure of blood oxygen and solubility of blood oxygen; and
(A6) calculating blood glucose concentration.

12. An image blood glucose concentration detecting method, adapted to the apparatus of claim 3, comprising following steps:
   (A1) emitting light beams of different wavelengths from a plurality of light sources to a skin;
   (A2) capturing images of the skin each respectively corresponding to each of the different wavelengths by receiving the light beams of different wavelengths reflected from the skin;
   (A3) detecting temperature of the skin;
   (A4) calculating blood oxygen saturation according to the images;
   (A5) transforming the blood oxygen saturation into partial pressure of blood oxygen and solubility of blood oxygen; and
   (A6) calculating blood glucose concentration.

13. An image blood glucose concentration detecting method, adapted to the apparatus of claim 4, comprising following steps:
   (A1) emitting light beams of different wavelengths from a plurality of light sources to a skin;
   (A2) capturing images of the skin each respectively corresponding to each of the different wavelengths by receiving the light beams of different wavelengths reflected from the skin;
   (A3) detecting temperature of the skin;
   (A4) calculating blood oxygen saturation according to the images;
   (A5) transforming the blood oxygen saturation into partial pressure of blood oxygen and solubility of blood oxygen; and
   (A6) calculating blood glucose concentration.

14. An image blood glucose concentration detecting method, adapted to the apparatus of claim 5, comprising following steps:
   (A1) emitting light beams of different wavelengths from a plurality of light sources to a skin;
   (A2) capturing images of the skin each respectively corresponding to each of the different wavelengths by receiving the light beams of different wavelengths reflected from the skin;
   (A3) detecting temperature of the skin;
   (A4) calculating blood oxygen saturation according to the images;
   (A5) transforming the blood oxygen saturation into partial pressure of blood oxygen and solubility of blood oxygen; and
   (A6) calculating blood glucose concentration.

15. An image blood glucose concentration detecting method, adapted to the apparatus of claim 6, comprising following steps:
   (A1) emitting light beams of different wavelengths from a plurality of light sources to a skin;
   (A2) capturing images of the skin each respectively corresponding to each of the different wavelengths by receiving the light beams of different wavelengths reflected from the skin;
   (A3) detecting temperature of the skin;
   (A4) calculating blood oxygen saturation according to the images;
   (A5) transforming the blood oxygen saturation into partial pressure of blood oxygen and solubility of blood oxygen; and
   (A6) calculating blood glucose concentration.

* * * * *